United States Patent [19]

Wakabayashi et al.

[11] Patent Number: 5,519,011
[45] Date of Patent: *May 21, 1996

[54] FOOD COMPOSITE PERFORMING FUNCTION OF IMPROVING SERUM LIPID

[75] Inventors: Shigeru Wakabayashi, Sanda; Mitsuko Satouchi, Takarazuka; Kazuhiro Ohkuma, Sanda, all of Japan

[73] Assignee: Matsutani Chemical Industries Co., Ltd., Hyogo, Japan

[*] Notice: The term of this patent shall not extend beyond the expiration date of Pat. No. 5,364,652.

[21] Appl. No.: 314,255

[22] Filed: Sep. 29, 1994

Related U.S. Application Data

[62] Division of Ser. No. 73,621, Jun. 8, 1993, abandoned, which is a continuation of Ser. No. 879,134, May 5, 1992, abandoned, which is a continuation of Ser. No. 659,949, Feb. 26, 1991, abandoned.

[30] Foreign Application Priority Data

Feb. 26, 1990 [JP] Japan ........................ 2-46647

[51] Int. Cl.⁶ .................................................. C08B 30/18
[52] U.S. Cl. ............................ 514/58; 127/33; 435/96
[58] Field of Search .......................... 127/33, 40; 435/74, 435/95, 97, 101, 103, 96; 514/58

[56] References Cited

U.S. PATENT DOCUMENTS

| | | | |
|---|---|---|---|
| 2,494,191 | 1/1950 | Neumann | 536/102 |
| 3,086,008 | 4/1963 | Opila et al. | 536/103 |
| 3,974,032 | 8/1976 | Harjes et al. | 426/661 |
| 5,344,824 | 9/1994 | Ohkuma et al. | |
| 5,364,652 | 11/1994 | Ohkuma et al. | 426/658 |

FOREIGN PATENT DOCUMENTS

| | | |
|---|---|---|
| 0368451 | 5/1990 | European Pat. Off. |
| 0443788 | 8/1991 | European Pat. Off. |
| 0443789 | 8/1991 | European Pat. Off. |

OTHER PUBLICATIONS

"Grant and Hackh's Chemical Dictionary", fifth edition, p. 484 (1987).
Chemical Abstracts, vol. 84, No. 20, May 17, 1976, p. 118, Abstract No. 137552k.
Chemical Abstracts, vol. 109, No. 11, Sep. 12, 1988, p. 99, Abstract No. 95048c.
Patent Abstracts of Japan, vol. 8, No. 77 (C–218)(1514), Apr. 10, 1984.
Patent Abstracts of Japan, vol. 13, No. 384 (C–629)(3732), Aug. 24, 1989.

*Primary Examiner*—Jeffrey Mullis
*Attorney, Agent, or Firm*—Sughrue, Mion, Zinn, Macpeak & Seas

[57] ABSTRACT

A method for decreasing a content of lipid and total cholesterol in serum and increasing a relative content of HDL cholesterol in serum which comprises the steps:

(a) providing a pyrodextrin hydrolysate which is obtained by heating starch in the presence of an acid and hydrolyzing the pyrodextrin with α-amylase; and (b) administering an effective amount of the pyrodextrin hydrolysate to an animal.

11 Claims, 4 Drawing Sheets

FOOD COMPOSITE PERFORMING FUNCTION OF IMPROVING SERUM LIPID

This is a Divisional of Application No. 08/073,621, filed Jun. 8, 1993, which is a Continuation of 07/879,134, filed May 5, 1992, which in turn is a Continuation of 07/659,949, filed Feb. 26, 1991, all abandoned.

BACKGROUND OF THE INVENTION

1. Field of the Invention

The present invention relates to a food composite capable of performing a function of improving serum lipid.

In the invention, the term "function of improving serum lipid" means:

(1) a function of reducing serum lipid and total cholestrol in serum; and (2) a function of improving serum lipo-protein metabolism.

2. Description of Prior Art

Increases in serum lipid and cholesterol in serum and decrease in the relative content of HDL-cholesterol called benign cholesterol, can be said to be malignant factors for various circulatory diseases, such as arteriosclerosis, cerebral infarction or adult diseases such as, obesity, diabetes or the like.

It is also a recent trend in Japan that the rate of occurrence of the mentioned diseases has sharply increased with the westernization of foods for meals. The invention intends to provide a food composite performing the function of decreasing serum lipid and cholesterol in serum while increasing the relative content of HDL-cholesterol.

Hitherto, dietary fibers have been well known as material performing the function of decreasing the mentioned serum lipid, etc. Generally, dietary fibers are divided into water-soluble dietary fibers and insoluble ones, and their typical physiological functions have been reported as follows:

(1) function of reducing cholesterol in serum and liver;

(2) function of saving increase of blood glucose;

(3) function of regulating large bowel; and the like.

Among the above functions, it is generally said that function (1) is effective for preventing various disorders caused by the negative relation between intestinal flora and metabolite, abdominal inflation, restraint of absorbing nutritious material, inhibition of circulation through bowel and liver, and so on. It is also said, however, that in the case of these dietary fibers, the insoluble fibers represented by cellulose have a disadvantage in view of taste and texture, and that, though the soluble fibers represented by guar gum and pectin are certainly advantageous in view of performing such useful physiological function of saving increase of blood glucose and inhibition of cholesterol, they have also a disadvantage of giving a negative affect on the absorption of useful metals. Moreover, because of high viscosity, there arises a further disadvantage of making it difficult to take them in a large quantity and, as a result, uses of these fibers are quite limited.

As noted above, westernization and diversification of meals have taken place in Japan and the mentioned diseases have been increasing.

The inventors of the present application have noticed the existence of pyrodextrin that has never been considered as a food material and, after having repeated studies and tests on whether or not pyrodextrin inhibits the performance of serum lipid, have come to reach a new idea of developing a novel food composite capable for performing such a function as improving serum lipid.

SUMMARY OF THE INVENTION

Accordingly, an object of the present invention is to develop and provide a novel food composite being capable of performing a function of improving serum lipid from pyrodextrin based on the mentioned new idea.

The foregoing object of the invention is accomplished by employing a refined product of pyrodextrin that can be obtained through a process wherein starch or starch hydrolyzate is decomposed by heating in the presence of an acid or without an acid, the mentioned refined pyrodextrin serving as a main components of the food composites performing a function of improving serum lipid.

As mentioned above, the invention is based on a novel concept that the refined pyrodextrin obtained through the process of decomposing at least one of starch or starch hydrolyzate exhibits an extremely remarkable function of improving serum lipid, more specifically, the mentioned functions of (1) and (2).

Described now is a process for preparing pyrodextrin in accordance with the invention.

As for a raw starch, that is, a starch to be employed in embodying the invention, a wide range of starches such as potato, corn, and cassaba can be utilized. It is also preferable to employ those starches in the form of processed food commercially available in the market. In this case, examples of processed starches are, for example, soluble starch, esterified starch, etherized starch, cross-linked starch and, preferably, starch phosphate and hydroxypropyl starch.

Furthermore, as a material employed in embodying the invention, starch hydrolyzate is used rather than the starches mentioned above. This starch hydrolyzate is obtained by slightly hydrolyzing a starch, and in such hydrolyzation, acid or enzyme may be added. The degree of hydrolyzation of starch should be in the range of DE3 to DE4, and the added acid should be normally oxalic acid or hydrochloric acid with their amount in the range of 0.01% to 0.1% (in terms of the weight of starch). In addition, α-amylase can be used as an enzyme.

These raw materials, in accordance with the invention, are decomposed by heating, preferably, under normal pressure. The decomposition by heating is achieved by heating the materials at a temperature from about 150° C. to 220° C. for 1 to 5 hours. The pressure at heating may be ambient without any necessity of either vacuum or additional pressure. At this heating step, it is also preferable to add an acid as a catalyst for heating decomposition. As the acid to be adopted as the catalyst, mineral acids such as sulfuric acid, hydrochloric acid, and nitric acid can be used, and in particular, hydrochloric acid is preferable when added in an amount of several % by weight to the materials to have a concentration of 1% by weight. The acid should be added evenly, preferably being well mixed by spraying. The mixture is then preferably preliminarily dried at a temperature of from about 100° C. to 120° C. so as to reduce the moisture to about 5%.

The dextrin, in accordance with the invention, obtained in the mentioned process, that is, pyrodextrin, is then subject to refining. The refining process is now described hereunder:

At least one treatment selected from treatments (a) and (b) is employed:

(a) After hydrolysis with α-amylase, or after hydrolysis with glucoamylase following the hydrolysis with α-amylase, the solution is refined through known processes of filtration, decolorization, and deionization.

(b) After completing treatment (a), a further treatment separates the dextrin fraction with chromatography by ion-exchanger resins.

A further description of treatments (a) and (b) is given in detail as follows:

In treatment (a), pyrodextrins are dissolved in water to obtain a solution of 30% to 50% by weight, and then neutralized to pH 5.5 to 6.5, preferably to pH 5.8, and 0.05% to 0.2% by weight of α-amylase (available in the market, either the one originated from mold or the one from bacteria may be applied) based on the pyrodextrin is added to the solution, and then at the reaction temperature of said amylase in the range from about 85° C. to 100° C., the solution is hold for 30 minutes to 2 hours. Subsequently, the temperature of the solution is raised up to 120° C. to complete the reaction of α-amylase. There-after, the temperature of the solution is decreased to about 55° C., and the solution is adjusted to about pH 5.5, then 0.05% to 0.2% by weight of glucoamylase (popularly used) based on the original dextrin is added. The solution is kept at said temperature to allow its reaction for 24 to 48 hours. This reaction aims at decomposition of small molecules such as oligosaccharides into glucose. Following this the, temperature of the solution is raised up to, for example, about 80° C. to complete the reaction of glucoamylase.

On the other hand, in treatment (b), chromatographic separation by ion-exchange resin is carried out. In this treatment, strongly acidic cation exchange resins sold widely on the market can be employed.

Preferable, as concrete examples, are Amberlite IR-116, IR-118, IR-120B, XT-1022E, XT-471F (all manufactured by Organo), Diaion SK-1B, SK-102, SK-104, SK-106, SK-110, SK-112, SK-116, FR-01 (all manufactured by Mitsubishi Chemicals), and XFS-43281.00, XFS-43280.00, XFS-43279.00, XFS-43278.00 (all manufactured by Dow Chemicals).

These resins are preferably dealt with as alkaline metal type or alkaline earth metal type before their uses. It is preferable to adjust the rate of flow at the time of the column fluid according to a resin to be used. The rate of flow of the fluid is preferably in the range of SV=0.1 to 0.6. The rate of flow out of the above range tends to deteriorate the workability and separation. The temperature at the time of running the fluid is preferably in the range from 20° C. to 70° C., and a temperature below this range will deteriorate the separation and make the viscosity of fluid get high, thereby giving a negative influence on the fluid, while a temperature exceeding this range will cause the fluid to be colored and deteriorate other quality characteristics.

When observing carefully the dextrin refined from the mentioned pyrodextrin, it was recognized that their linkages were not only 1→4 and 1→6 bonds with glucose as a structural sugar, but also 1→2 and 1→3 bonds. Further, a part of the reducing end group is 1-6-anhydro-glucose.

The viscosity of this pyrodextrin is rather low, i.e., about 10 cps (30%, 30° C.), and it tastes slightly sweet and is odorless, with the number of 1→2 and 1→3 bonds below about 10%. The pyrodextrin is, therefore, easily employed as a material for various beverages and processed foods and, furthermore, it is as safe to be eaten as maltodextrin, since its raw material is starch.

In this manner, the pyrodextrin serving as the above food material in accordance with the invention can be widely used as a material for various foods, and its uses extend to any food so far as it is used as a material for food. Typical foods in this sense are, for example, beverages, desserts and candies.

Other objects, features and advantages of the invention will become apparent in the course of the following description accompanied by the drawings.

BRIEF DESCRIPTION OF THE DRAWINGS

FIGS. 1 to 7 are graphs showing the results of measuring the function of improving serum lipid on the food composites of rats, and wherein, FIG. 1 shows of accumulated intake amount of water;

FIG. 2 shows change of body;

FIG. 3 shows change of total protein in blood;

FIG. 4 shows change of calcium in blood;

FIG. 5 shows change of triglyceride in blood;

FIG. 6 shows change of total cholesterol (solid line) and HDL-cholesterol (dot line) in blood; and FIG. 7 shows change of HDL-cholesterol division.

Throughout the drawings, marks indicate respectively as follows:

●: control

○: PF-C

▲: PF

*: $p<0.05$ (showing a level of significance of 5% with respect to the comparative reference by T test)

*: $p<0.02$ (showing a level of significance of 2% in the same test)

PF: a pyrodextrin hydrolysate obtained by a process wherein pyrodextrin is hydrolyzed with α-amylase, then is refined by decolorization with activated charcoal and deionization using ion exchange resins.

PF-C: a pyrodextrin hydrolysate obtained by a process wherein pyrodextrin is hydrolyzed with α-amylase and glucoamylase, then the glucose produced thereby is excluded by column chromatography.

DESCRIPTION OF THE PREFERRED EMBODIMENTS

Several examples in accordance with the present invention is hereinafter described in more detail.

Example 1

5-week-old male rats of SD strain (JAPAN CLEA) were put in separate cages and raised preliminarily for 10 days with ordinary solid feed. These rats were divided into three groups each being formed of 5 rats, then three kinds of solution, i.e., an aqueous solution of 10% PF, an aqueous solution of 10% PF-C and tap water were respectively given from feeding bottles to the rats as drinking water. The three groups of sample rats were free to take the feed and water in, and during the period from one week before starting this test until passing seven weeks therefrom, their intake amount of water, body weight, total protein, calcium, triglyceride, total cholesterol and HDL-cholesterol in blood were periodically measured by the following methods, respectively:

Total protein: by biurel method

Calcium: OCPC method

Triglyceride: enzyme method

Total cholesterol: enzyme method

Total HDL-cholesterol: enzyme method

Figure 1:
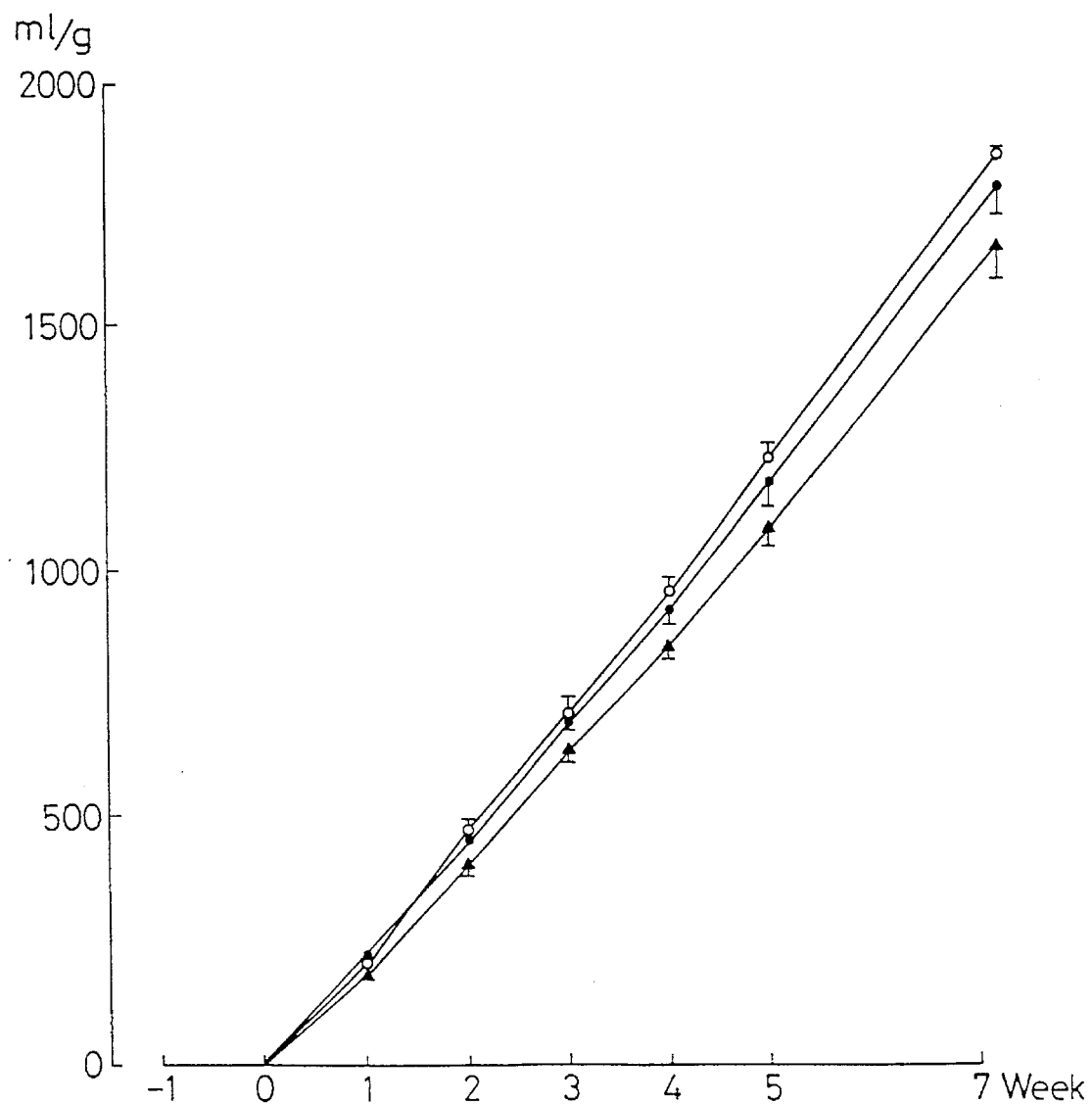
Figure 2:
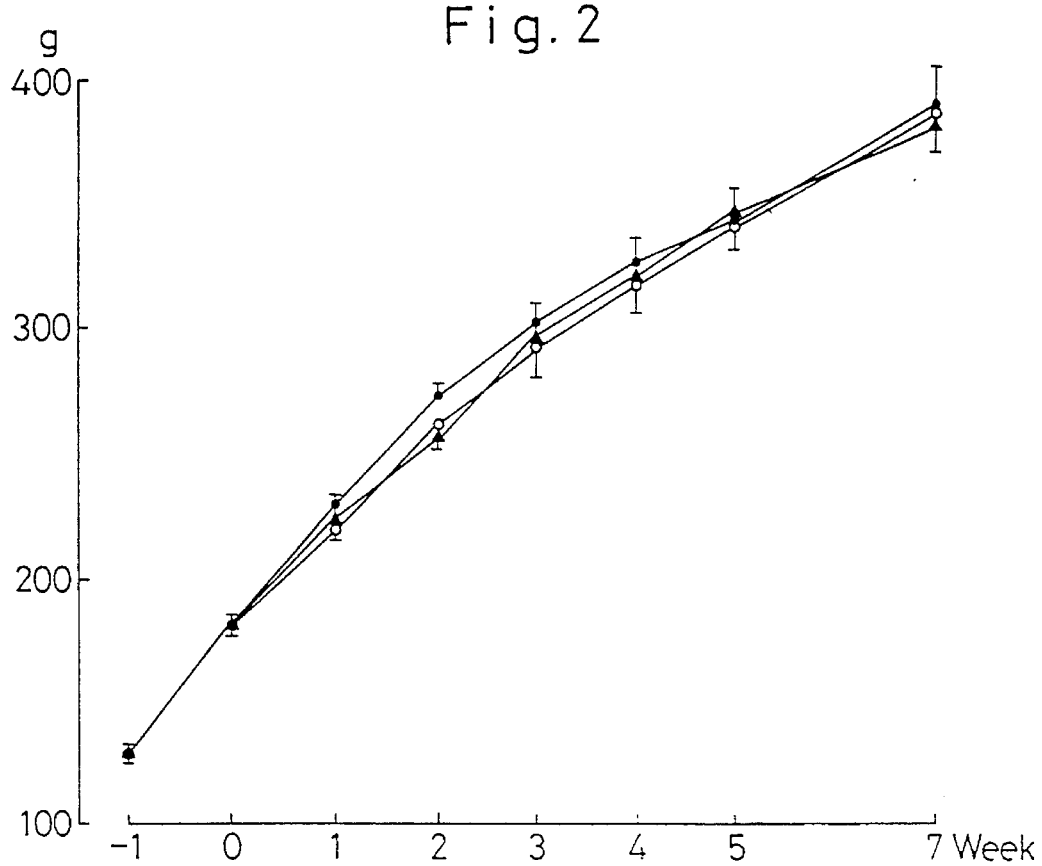
Figure 3:
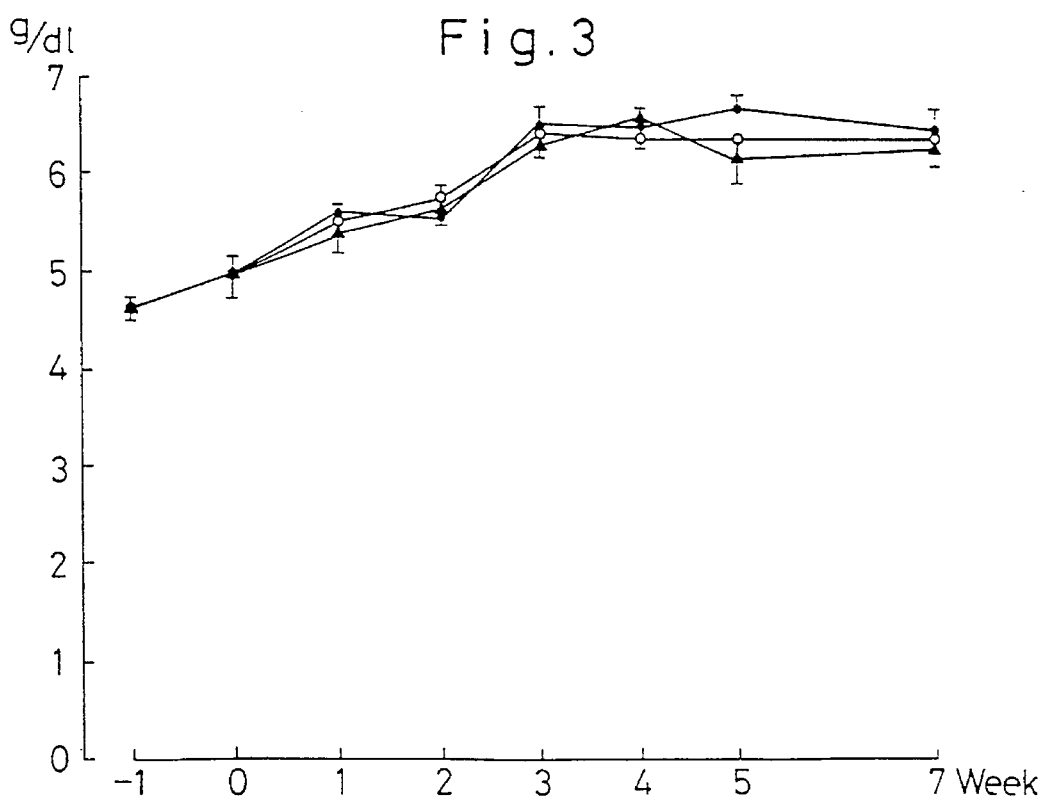
Figure 4:
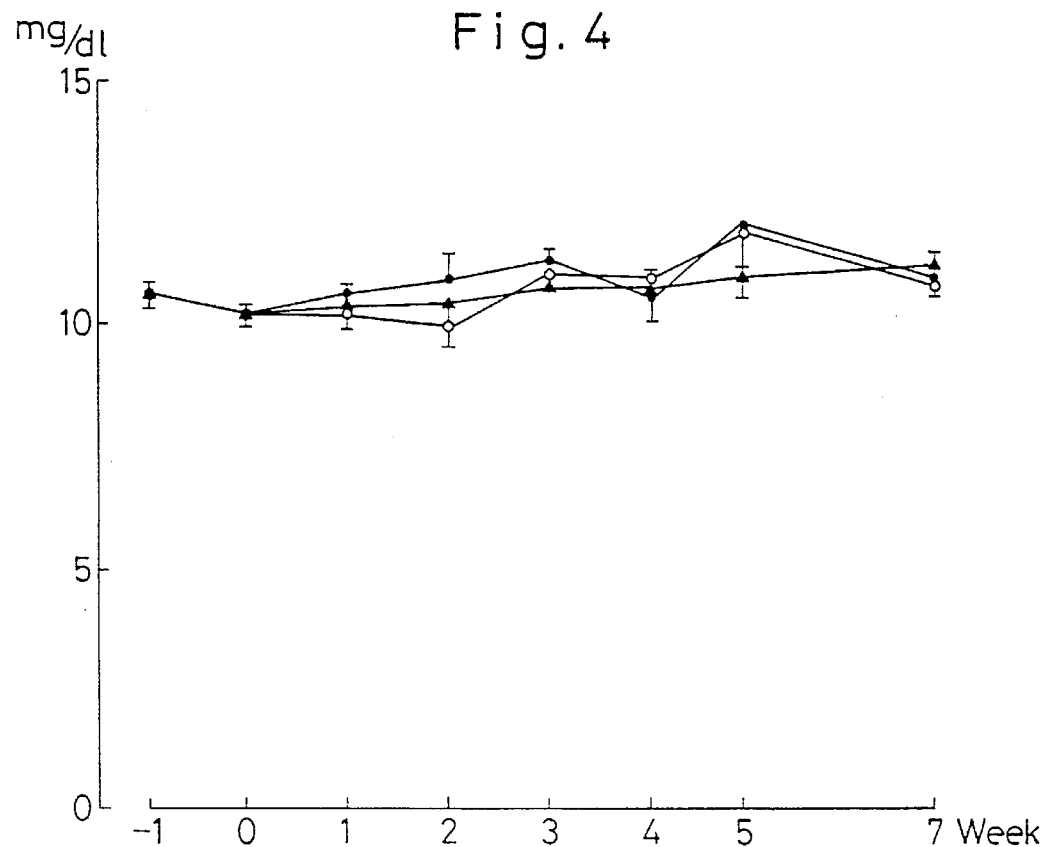
Figure 5:
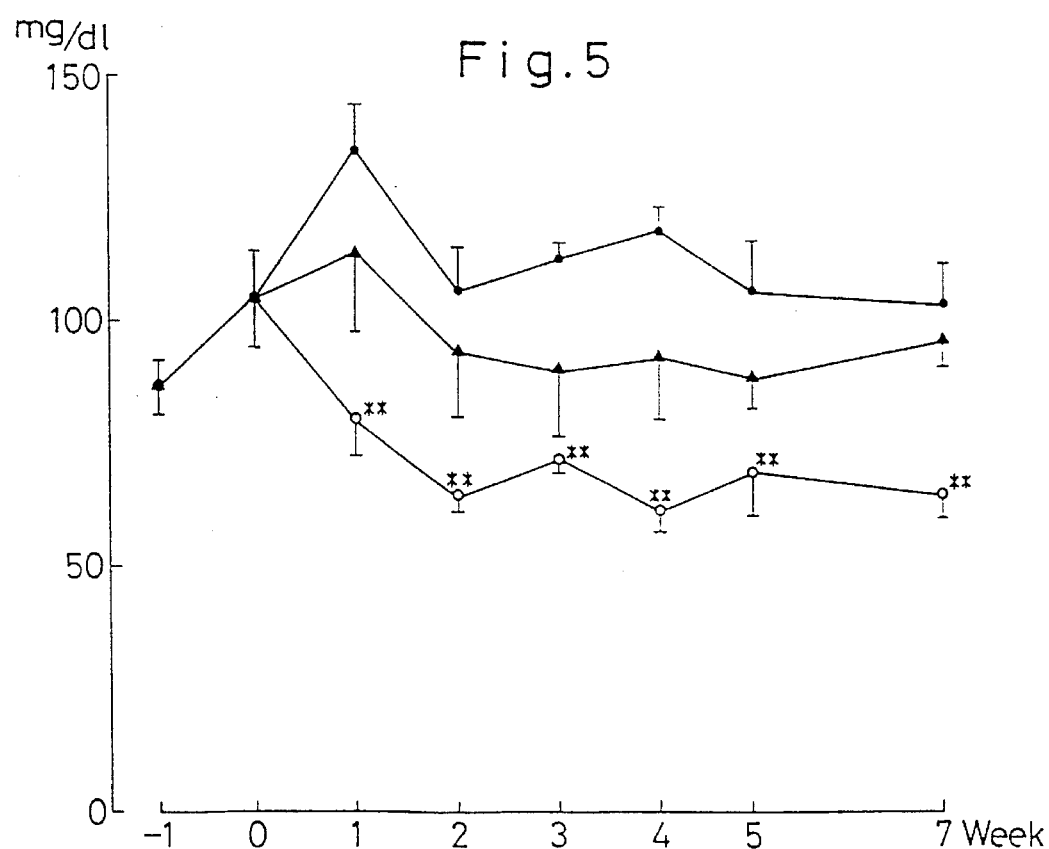
Figure 6:
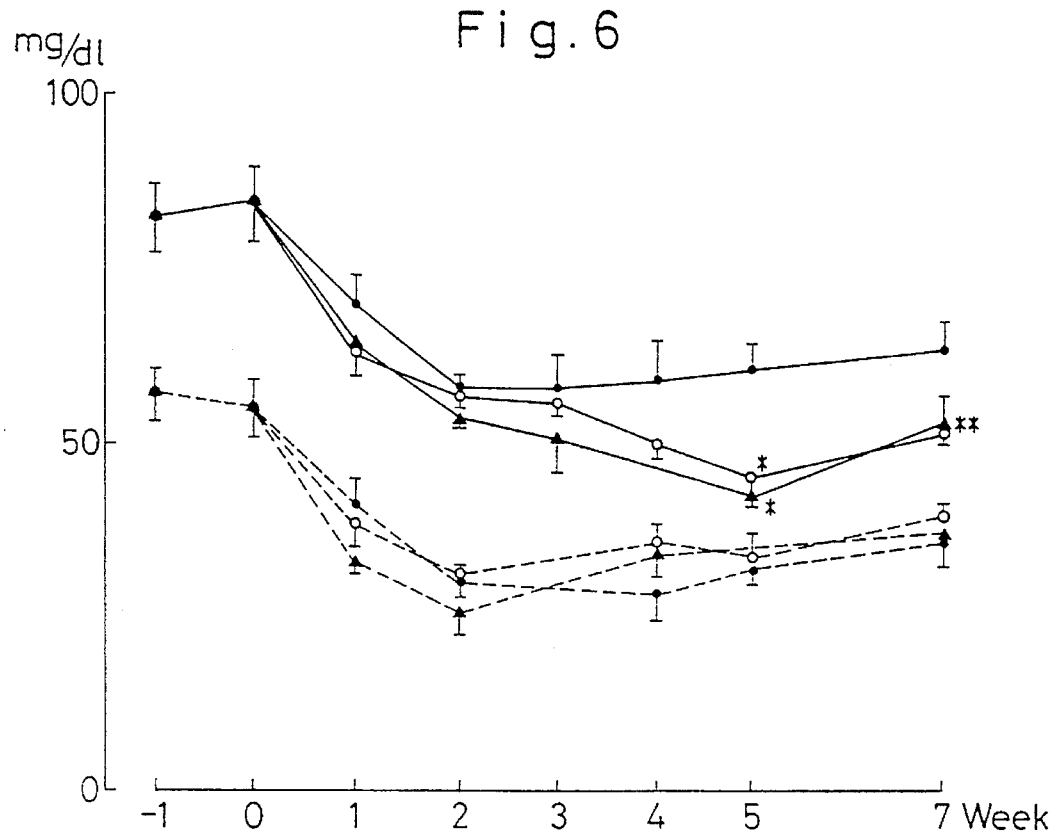
Figure 7:
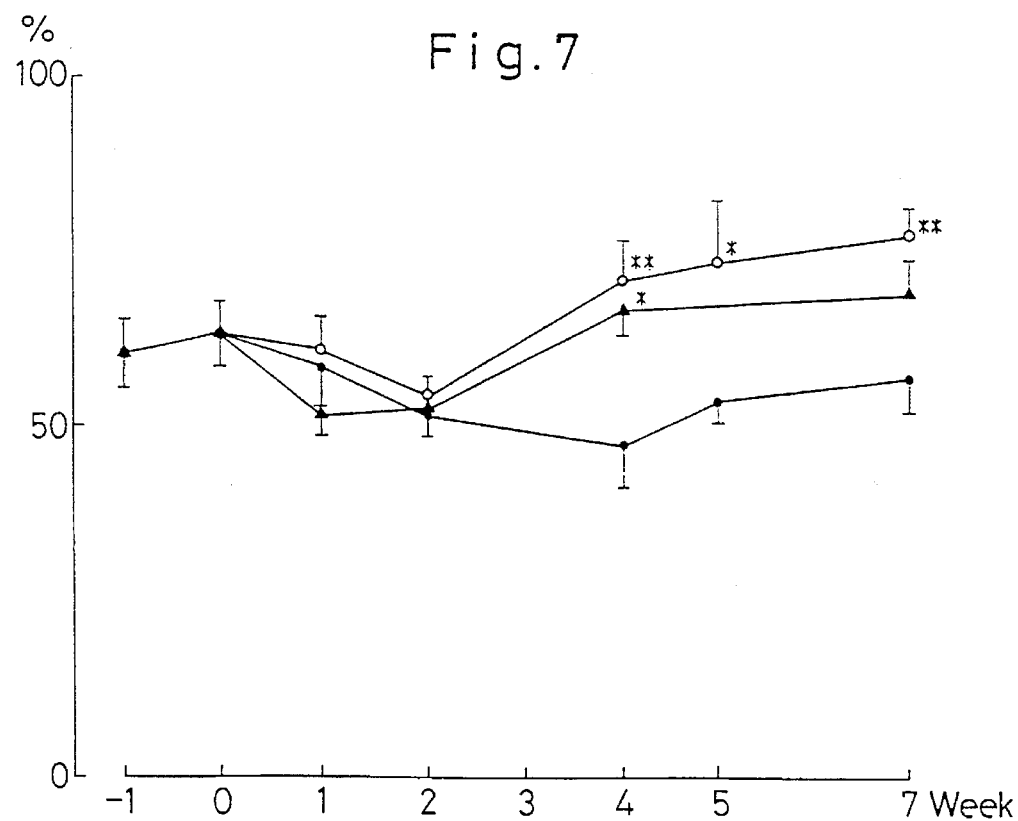

FIGS. 1 to 7 show the results of measurement, and in which each drawing, PF, and PF-C show the following, respectively:

FIG. 1: change of accumulated intake amount of water;
FIG. 2: change of body weight;
FIG. 3: change of total protein in blood;
FIG. 4: change of calcium in blood;
FIG. 5: change of triglyceride in blood;
FIG. 6: change of total cholesterol (solid line) and HDL-cholesterol (dot line) in blood; and
FIG. 7: change of HDL-cholesterol division.

Throughout the above drawings, average value ± standard error ($\bar{x}\pm$SEM) marks indicate, respectively, as follows:

●: control
○: PF-C
▲: PF
*: $p<0.05$ (showing a significant peril rate of 5% with respect to the comparative reference by T test)
*: $p<0.02$ (showing a significant peril rate of 2% in the same test)
PF: a pyrodextrin hydrolysate obtained by a process wherein pyrodextrin is hydrolyzed with α-amylase, then is refined by decolorization with activated charcoal and deionization using ion exchange resins.
PF-C: a pyrodextrin hydrolysate obtained by a process wherein pyrodextrin is hydrolyzed with α-amylase and glucoamylase, then the glucose produced thereby is excluded by column chromatography.

It is understood from FIG. 1 that there was no difference among the three groups of sample rats in the aspect of accumulated intake amount of water, and PF and PF-C were taken in without trouble.

It is understood from FIGS. 2 to 4 that there was no difference among the three groups of sample rats with respect to body weight, total protein and calcium values in blood, and thus it was acknowledged that neither PF nor PF-C gave a negative influence on the growth of the rats and absorption of mineral to be taken in safely.

It is understood from FIG. 5 that the triglyceride value of the sample rats belonging to the PF and PF-C intake group was definitely small as compared with the control group, and this advantage has been recognized throughout the entire period of the test.

It is understood from FIG. 6 that the total cholesterol value in blood has shown a reduction corresponding to the growth of the sample rats belonging to the control group up to the second week, then normal state has been kept up to the seventh week. On the other hand, the total cholesterol value in the PF and PF-C group has shown a sharp reduction up to the second week from the beginning of the test, and has further continued to reduce up to the fifth week. The total cholesterol values up to the fifth and seventh weeks were both significantly lower as compared with the control group. Concerning the HDL-cholesterol value in blood deeply involved in the prevention of arteriosclerosis and ischemic heart disease, no difference was acknowledged among the three groups. It is, however, understood from FIG. 7 that when calculating percentage of HDL-cholesterol occupied in total cholesterol, the PF and PF-C groups show higher percentages as compared with the control group, and an advantage of improvement in lipoprotein metabolism was recognized.

In this respect, it was reported by S. R. Srinivasan and others that when giving a meal of low saturation fat to Rhesus monkeys, etc., their serum cholesterol level is lowered as compared with a meal of dextrin in substitution for cane sugar. It has been heretofore well known that serum cholesterol levels go down easily by reducing the intake energy. On the other hand, cane sugar, in particular, fructose being a main component thereof, performs a function of increasing cholesterol and neutral fat. Accordingly, in the mentioned well-known method for cholesterol reduction, influence by cane sugar should not be ignored in spite of energetic equivalency. Consequently, in the foregoing embodiment in accordance with the present invention, solid feed commercially available in the market was given to every group of control and sample rats, and indigestible dextrin was dosed to the samples as drinking water in substitution for tap water in order to verify influence on the serum cholesterol and other clinical test values.

The invention may be embodied in other specific forms without departing from the spirit or essential characteristics thereof. The foregoing examples are therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A method for decreasing a content of lipid and total cholesterol in serum and increasing a relative content of HDL cholesterol in serum in a host which is in need of such decrease and increase which comprises the steps of:

(a) providing a pyrodextrin hydrolysate which is obtained by heating starch in the presence of hydrochloric acid in an amount of 0.01 to 0.1% by weight based on the weight of said starch at 150° C. to 220° C. for 1 to 5 hours to prepare pyrodextrin, hydrolyzing the pyrodextrin with alpha-amylase and then with glucoamylase by dissolving the pyrodextrin in water to form an aqueous solution in an amount of 30 to 50% by weight of pyrodextrin based on the weight of the solution, adjusting the pH of the solution to pH 5.5 to 6.5, treating the solution with alpha-amylase in an amount of 0.05 to 0 0.2% by weight based on the weight of the pyrodextrin at 85° C. to 100° C. for 0.5 to 2 hours, treating the solution with glucoamylase in an amount of 0.05 to 0.2% by weight based on the weight of the pyrodextrin at about 55° C. for 24 to 48 hours to obtain hydrolyzed pyrodextrin, refining the hydrolyzed pyrodextrin, and subjecting the hydrolyzed and refined pyrodextrin to ion exchange resin chromatography to separate said pyrodextrin hydrolysate; and (b) administering the pyrodextrin hydrolysate to an animal in an amount effective to bring about such decrease and increase.

2. The method of claim 1, wherein said animal is a human being.

3. The method of claim 2, wherein said pyrodextrin hydrolysate is administered in the form of food containing the same.

4. The method of claim 1, wherein said ion exchange resin is an alkaline metal or alkaline earth metal type of strongly acidic ion exchange resin.

5. The method of claim 1, wherein said pyrodextrin hydrolysate contains 1→4, 1→6, 1→2 and 1→3 linkages and a part of reducing terminal groups of said pyrodextrin hydrolysate are 1→6 anhydroglucose.

6. The method according to claim 1, wherein said refining comprises decolorization and deionization.

7. A method for decreasing a content of lipid and total cholesterol in serum and increasing a relative content of HDL cholesterol in serum in a host which is in need of such decrease and increase which comprises the steps of:

(a) providing a pyrodextrin hydrolysate which is obtained by heating starch in the presence of hydrochloric acid in an amount of 0.01 to 0.1% by weight based on the weight of said starch at 150° C. to 220° C. for 1 to 5 hours to prepare pyrodextrin, hydrolyzing the pyrodextrin with alpha-amylase by dissolving the pyrodextrin in water to form an aqueous solution in an amount of 30 to 50% by weight of pyrodextrin based on the weight of the solution, adjusting the pH of the solution to pH 5.5 to 6.5, treating the solution with alpha-amylase in an amount of 0.05 to 0.2% by weight based on the weight of the pyrodextrin at 85° C. to 100° C. for 0.5 to 2 hours to obtain hydrolyzed pyrodextrin, and refining the hydrolyzed pyrodextrin; and (b) administering the pyrodextrin hydrolysate to an animal in an amount effective to bring about such decrease and increase.

8. The method of claim 1, wherein said pyrodextrin hydrolysate contains $1 \rightarrow 4$, $1 \rightarrow 6$, $1 \rightarrow 2$ and $1 \rightarrow 3$ glucosidic linkages and a part of reducing terminal groups of said pyrodextrin hydrolysate are $1 \rightarrow 6$ anhydroglucose.

9. The method of claim 7, wherein said animal is human being.

10. The method of claim 9, wherein said pyrodextrin hydrolysate is administered in the form of food containing the same.

11. The method according to claim 7, wherein said refining comprises decolorization and deionization.

* * * * *